(12) United States Patent
Farrand

(10) Patent No.: US 6,511,719 B2
(45) Date of Patent: *Jan. 28, 2003

(54) CHIRAL COMPOUNDS

(75) Inventor: Louise Farrand, Manchester (GB)

(73) Assignee: Merck Patent Gesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/130,346

(22) Filed: Aug. 13, 1998

(65) Prior Publication Data

US 2002/0076510 A1 Jun. 20, 2002

(30) Foreign Application Priority Data

Aug. 13, 1997 (EP) .............................. 97113935

(51) Int. Cl.[7] .................. C09K 19/38; C09K 19/34; C09K 19/12; C09K 19/30; C07C 69/767; C07C 69/76; C07C 69/97

(52) U.S. Cl. .............. 428/1.1; 252/299.61; 252/299.63; 252/299.66; 560/65; 560/83; 560/128

(58) Field of Search ................ 252/299.01, 299.61, 252/299.62, 299.63, 299.66; 349/182; 560/65, 83, 128; 570/127, 128, 129, 131; 428/1.1

(56) References Cited

U.S. PATENT DOCUMENTS

| | | | |
|---|---|---|---|
| 4,988,458 A | 1/1991 | Heppke et al. | 252/299.63 |
| 5,093,027 A | 3/1992 | Kelly et al. | 252/299.63 |
| 5,411,676 A | 5/1995 | Kelly et al. | 252/299.63 |
| 5,676,879 A | * 10/1997 | Heynderickx et al. | 252/299.01 |
| 5,744,057 A | * 4/1998 | Meyer et al. | 252/299.01 |

FOREIGN PATENT DOCUMENTS

DE 3617826 * 4/1987

OTHER PUBLICATIONS

CAPLUS 1987: 449764.*
CAPLUS 1995: 947517.*
CA 76: 98569, 1971.*
CA 75: 48085, 1971.*
CA 78: 96841, 1972.*
CAPLUS 1996: 543373.*
Lipshutz et al., *Angew. Chem.,* vol. 106(18), pp. 1962–1964 (1994).
Lipshutz et al., *Tetrahedron Letters,* vol. 35(31), pp. 5567–5570 (1994).
Miyano et al., *Bull. Chem. Soc. Jpn.,* vol. 57, pp. 1943–1947 (1984).
Harada et al., *Enantiomer,* vol. 1, pp. 119–138 (1996).
Kelly et al., *Liquid Crystals,* vol. 11(5), pp. 761–771 (1992).
Kitzerow et al., *Liquid Crystals,* vol. 11(4), pp. 561–568 (1992).
Crosby et al., *Synthesis,* vol. 1, pp. 141–145 (1993).
Pini et al., *Synthesis,* vol. 11, pp. 1023–1024 (1990).
Dietl, et al., *Tetrahedron,* vol. 41(7), pp. 1193–1197 (1985).
Derwent Abstract of DE 3617826 A, 1987.

* cited by examiner

Primary Examiner—Shean C. Wu
(74) Attorney, Agent, or Firm—Millen, White, Zelano & Branigan, P.C.

(57) ABSTRACT

The invention relates to chiral compounds of formula I

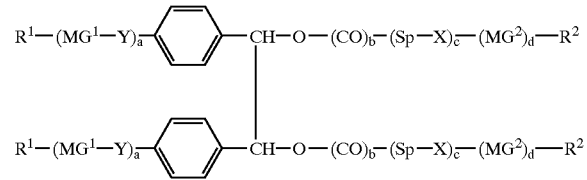

wherein $R^1$, $R^2$, $MG^1$, $MG^2$, Sp, X, Y, a, b, c and d have the meaning given in claim 1, to a liquid crystalline mixture comprising at least one chiral compound of formula I, to a polymerizable liquid crystalline mixture comprising at least one chiral compound of formula I and optionally at least one polymerizable mesogenic compound, to the use of such a liquid crystalline mixture or a polymerizable liquid crystalline mixture for the preparation of anisotropic polymer films with a chiral liquid crystalline phase, for active and passive optical elements like polarizers, compensators or color filters and for liquid crystal displays, for example STN, TN, AMD-TN, temperature compensation, guest-host or phase change displays, or surface stabilized or polymer stabilized cholesteric texture (SSCT, PSCT) displays, to cholesteric liquid crystal displays comprising liquid crystalline mixtures comprising chiral compounds of formula I and to polymer films with a chiral liquid crystalline phase obtainable by (co)polymerizing a liquid crystalline mixture comprising at least one chiral compound of formula I and at least one polymerizable compound.

26 Claims, No Drawings

CHIRAL COMPOUNDS

The invention relates to chiral compounds of formula I

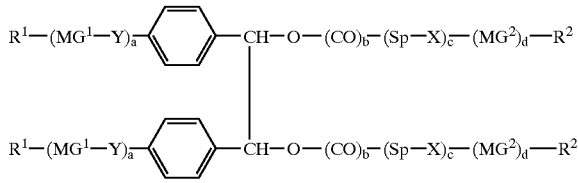

wherein
Sp in each case independently denotes a spacer group with up to 20 C atoms,
X in each case independently denotes —O—, —S—, —CO—, —COO—, —OCO—, —OCO—O—, —CO—NH—, —NH—CO—, —OCH$_2$—, —CH$_2$O—, —SCH$_2$—, —CH$_2$S— or a single bond,
Y in each case independently denotes —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond,
a, b, c and d are in each case independently 0 or 1, provided that each a and d are not at the same time 0, (i.e., there must be at least one MG$^1$ or MG$^2$ group)
R$^1$ and R$^2$ are independently of each other H, CN, halogen or a straight-chain or branched alkyl radical with up to 25 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or alternatively are denoting P-(Sp-X)$_n$-, with Sp and X having the meanings given above, n being 0 or 1 and P being a polymerizable group, and
MG$^1$ and MG$^2$ are each independently a mesogenic or mesogenity supporting group, preferably selected of formula II

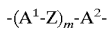 II with
Z denoting —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond,
A$^1$ and A$^2$ being in each case independently 1,4-phenylene in which, in addition, one or more CH groups may be replaced by N, 1,4-cyclohexylene in which, in addition, one or two non-adjacent CH$_2$ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or Cl, and
m being 0, 1, 2 or 3.

The invention also relates to a liquid crystalline mixture containing at least one chiral compound of formula I.

The invention also relates to a polymerizable liquid crystalline mixture comprising at least one chiral compound of formula I and at least one polymerizable mesogenic compound.

The invention furthermore relates to the use of such liquid crystalline mixtures for the preparation of anisotropic polymer films with a chiral liquid crystalline phase, for active and passive optical elements like polarizers, compensators or color filters and for liquid crystal displays, for example STN, TN, AMD-TN, temperature compensation, guest-host or phase change displays, or surface stabilized or polymer stabilized cholesteric texture (SSCT, PSCT) displays.

The invention also relates to liquid crystal displays comprising a liquid crystalline mixture or a polymerized liquid crystalline mixture and at least one chiral compound of formula I, and to polymer films with a chiral liquid crystalline phase obtainable by (co)polymerizing a liquid crystalline mixture comprising at least one chiral compound of formula I and at least one polymerizable mesogenic compound.

Upon further study of the specification and appended claims, further objects and advantages of this invention will become apparent to those skilled in the art.

BACKGROUND OF THE INVENTION

Chiral compounds can be used as dopants to induce or enhance a helical twist of the molecules of a liquid crystalline mixture that can be used for example in liquid crystal displays. The pitch p of the molecular helix in the first approximation, which is sufficient for most practical applications, is inversely proportional to the concentration c of the chiral dopant in the liquid crystal host mixture according to equation (1):

$$p = \frac{1}{HTP} \cdot \frac{1}{c} \quad (1)$$

The proportionality factor is the helical twisting power (HTP) of the chiral dopant.

For many applications it is desirable to have LC mixtures that exhibit a twist. Among these are e.g. phase-change displays, guest-host displays, passive and active matrix TN and STN displays like AMD-TN, including such displays with temperature compensated characteristics, e.g. by appropriate selection of the cholesteric compounds according to the invention either alone or in combination with further chiral dopants. For these applications it is advantageous to have available a chiral dopant with a high HTP in order to reduce the amount of dopant needed to induce the desired pitch.

For some applications it is desired to have LC mixtures that exhibit a strong helical twist and thereby a short pitch length. For example in liquid crystalline mixtures that are used in selectively reflecting cholesteric displays, the pitch has to be selected such that the maximum of the wavelength reflected by the cholesteric helix is in the range of visible light. Another possible application are polymer films with a chiral liquid crystalline phase for optical elements, such as cholesteric broadband polarizers or chiral liquid crystalline retardation films.

As can be seen from equation (1), a short pitch can be achieved by using high amounts of dopant or by using a dopant with a high HTP.

However, the chiral dopants of the prior art often exhibit low values of the HTP, so that high amounts of dopant are needed. This is a disadvantage because, as chiral dopants can be used only as pure enantiomers, they are expensive and difficult to synthesize.

Furthermore, and in many cases even more important, when using chiral dopants of prior art in high amounts, they often negatively affect the properties of the liquid crystalline host mixture, such as e.g. the dielectric anisotropy $\Delta\epsilon$, the viscosity, the driving voltage or the switching times.

Thus, there is a considerable demand for chiral compounds with a high HTP which are easy to synthesize, which can be used in low amounts, show improved temperature stability of the cholesteric pitch, e.g., for utilizing a constant reflection wavelength, and do not affect the properties of the liquid crystalline host mixture.

SUMMARY OF THE INVENTION

The invention has an aim of providing chiral compounds having these properties, but which do not have the disadvantages of the chiral dopants of the state of the art as discussed above.

Another aim of the invention is to extend the pool of chiral compounds that can be used as dopants available to the expert.

It has been found that these aims can be achieved by the provision of chiral compounds according to formula I.

The inventive chiral compounds contain a chiral structure element based on hydrobenzoin, which bears several advantages. For instance, the hydrobenzoin group exhibits two centers of chirality and thus leads to chiral compounds with a high twisting power. Also, enantiomerically pure hydrobenzoins are easy to prepare from cheap, readily available starting materials. The preparation methods are also suitable for large scale production. Furthermore, it is possible to prepare both the R,R and S,S enantiomers. This allows the preparation of chiral compounds that can induce a cholesteric phase with either a right or a left handed helix. The availability of both helices can be a considerable advantage, e.g., for the use in security film applications.

Chiral compounds comprising a hydrobenzoin structure unit and a mesogenic monocarboxylic acid rest with directly linked rings are disclosed in the DE 3534777 A1. The DE 3617826 A1 discloses chiral compounds of a broad generic formula that, among many other possible groups, may also comprise a hydrobenzoin group, but gives no hint to specific compounds except those mentioned in the DE 3534777 A1. The EP 415 220 B1 discloses chiral compounds that among others may comprise a hydrobenzoin structure unit, but is limited to mesogenic groups with long bridging groups between the rings.

Thus an object of this invention is chiral compounds of formula I

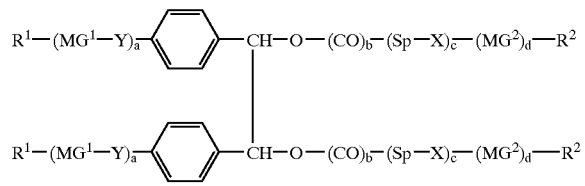

wherein
Sp in each case independently denotes a spacer group with up to 20 C atoms,
X in each case independently —O—, —S—, —CO—, —COO—, —OCO—, —OCO—O—, —CO—NH—, —NH—CO—, —OCH$_2$—, —CH$_2$O—, —SCH$_2$—, —CH$_2$S— or a single bond,
Y in each case independently —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond,
a, b, c and d are independently 0 or 1, with each pair of a and d not being at the same time 0,
$R^1$ and $R^2$ are independently of each other H, CN, halogen or a straight-chain or branched alkyl radical with up to 25 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or alternatively are denoting P-(Sp-X)$_n$-, with Sp and X having the meanings given above, n being 0 or 1 and P being a polymerizable group, and
$MG^1$ and $MG^2$ are each independently a mesogenic or mesogenity supporting group, preferably selected of formula II -(A$^1$-Z)$_m$-A$^2$-     II with
Z denoting —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond,
$A^1$ and $A^2$ being in each case independently 1,4-phenylene in which, in addition, one or more CH groups may be replaced by N, 1,4-cyclohexylene in which, in addition, one or two non-adjacent CH$_2$ groups may be replaced by O and/or S, 1,4-cyclohexenylene, 1,4-bicyclo(2,2,2)octylene, piperidine-1,4-diyl, naphthalene-2,6-diyl, decahydro-naphthalene-2,6-diyl, or 1,2,3,4-tetrahydronaphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or Cl, and
m being 0, 1, 2 or 3.
Another object of the invention is a liquid crystalline mixture containing at least one chiral compound of formula I.

Another object of the invention is a polymerizable liquid crystalline mixture comprising at least one chiral compound of formula I and at least one polymerizable mesogenic compound.

A further object of the invention is the use of a liquid crystalline mixture or a polymerizable liquid crystalline mixture as described above for the preparation of anisotropic polymer films with a chiral liquid crystalline phase, for active and passive optical elements like polarizers, compensators or color filters, and for liquid crystal displays, for example STN, TN, AMD-TN, temperature compensation, guest-host or phase change displays, or surface stabilized or polymer stabilized cholesteric texture (SSCT, PSCT) displays.

Another object of the invention is cholesteric liquid crystal displays comprising a liquid crystalline mixture or a polymerized liquid crystalline mixture comprising at least one chiral compound of formula I.

Yet another object of the invention is anisotropic polymer films with a chiral liquid crystalline phase obtainable by (co)polymerizing a liquid crystalline mixture comprising at least one chiral compound of formula I and at least one polymerizable mesogenic compound.

The term "mesogenity supporting group" as used in the foregoing and the following is indicating a rod-shaped, board-shaped or disk-shaped group, which does not necessarily have to show mesogenic behavior (i.e., the ability to introduce mesophase behavior in a compound comprising such a group) alone. It is also possible that such a group shows mesogenic behavior when combined in a compound with other groups, or if the compound comprising the mesogenity supporting group is polymerized or admixed with other compounds comprising the same or other types of mesogenic or mesogenity supporting groups.

The compounds of formula I are preferably selected from those of the following formulae

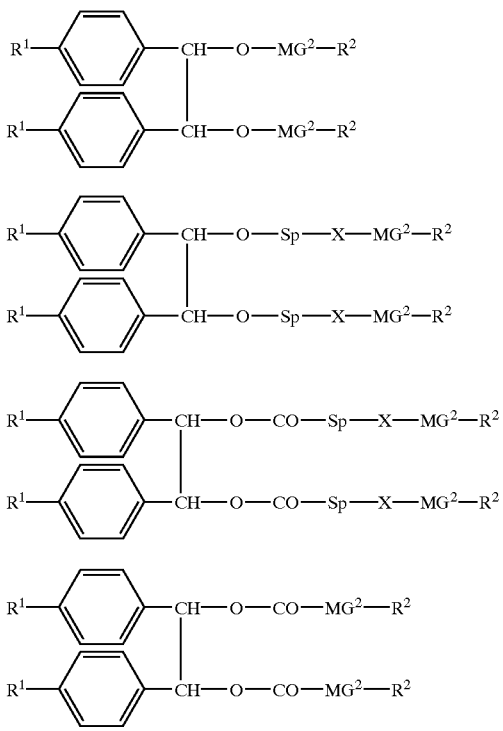

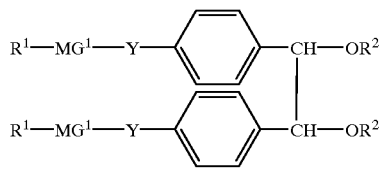

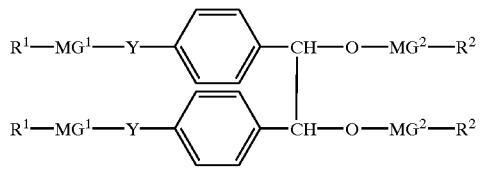

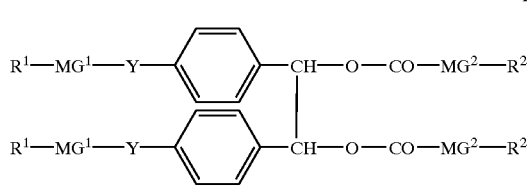

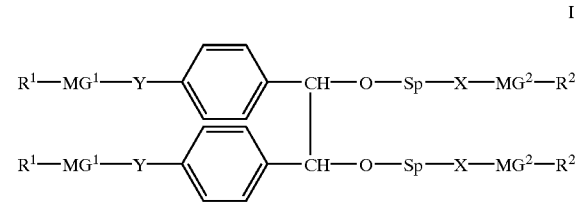

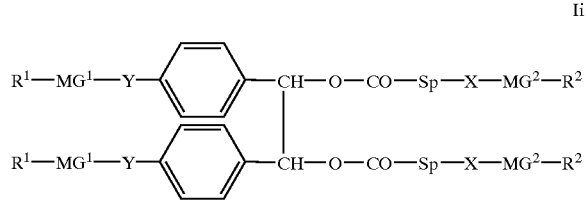

wherein $R^1$, $R^2$, $MG^1$, $MG^2$, X, Y and Sp have the meaning of formula I.

Of these compounds, particularly preferred are those of formula Ia, Ib, Ic, Ie, If and Ig, especially those of formula Ia, Ib, Ie and If.

Preferred compounds of formula Ia to Id are those wherein $R^1$ is H.

Further preferred are compounds of formula Ia to Ii wherein at least one of the groups $R^1$ and/or $R^2$ is denoting P-(Sp-X)$_n$-, with P, Sp, X and n having the meaning given in formula I.

Of the compounds of formula Ie to Ii especially preferred are those wherein $MG^1$ incorporates one or two six-membered rings.

Of the compounds of formula If and Ig especially preferred are those wherein $MG^2$ and $MG^1$ are selected such that $MG^2$ and the radical

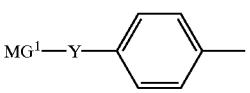

are identical.

Further preferred are compounds of formula Ic, Id, Ig and Ii in which $MG^2$ is selected of formula II wherein, if m is 1, Z is not a single bond, or, if m is 2 or 3, at least two of the groups Z are not a single bond.

Of the chiral compounds of formula I especially preferred are those in which $R^1$ and $R^2$ are F, Cl, cyano, alkyl or alkoxy and $MG^1$ and $MG^2$ are of formula II wherein Z is —COO—, —OCO—, —CH$_2$—CH$_2$—, —CH=CH—COO—, —OCO—CH=CH— or a single bond.

Particularly preferred compounds of formula I are those wherein $MG^1$ and $MG^2$ are essentially consisting of 1,4-phenylene and/or trans-1,4-cyclohexylene rings that are unsubstituted or substituted in 1 to 4 positions with F, Cl, CN or alkyl, alkoxy or alkanoyl with 1 to 4 C-atoms. From these preferred compounds, especially preferred are those wherein $MG^1$ and $MG^2$ are essentially consisting of biphenyl and cyclohexylphenyl groups.

A smaller group of preferred mesogenic groups $MG^1$ and $MG^2$ of formula II is listed below. For reasons of simplicity, Phe in these groups is 1,4-phenylene, PheL is a 1,4-phenylene group which is substituted by at least one group L, with L being F, Cl, CN or an optionally fluorinated alkyl, alkoxy or alkanoyl group with 1 to 4 C atoms, and Cyc is 1,4-cyclohexylene. The group of preferred mesogenic groups $MG^1$ and $MG^2$ of formula II comprises those of the formulae II-1 to II-27 as well as their mirror images

| | |
|---|---|
| -Phe- | II-1 |
| -Cyc- | II-2 |
| -PheL- | II-3 |
| -Phe-Z-Phe- | II-4 |
| -Phe-Z-Cyc- | II-5 |
| -Cyc-Z-Cyc- | II-6 |
| -PheL-Z-Phe- | II-7 |
| -PheL-Z-Cyc- | II-8 |
| -PheL-Z-PheL- | II-9 |
| -Phe-Z-Phe-Z-Phe- | II-10 |
| -Phe-Z-Phe-Z-Cyc- | II-11 |
| -Phe-Z-Cyc-Z-Phe- | II-12 |
| -Cyc-Z-Phe-Z-Cyc- | II-13 |
| -Phe-Z-Cyc-Z-Cyc- | II-14 |
| -Cyc-Z-Cyc-Z-Cyc- | II-15 |
| -Phe-Z-Phe-Z-PheL- | II-16 |
| -Phe-Z-PheL-Z-Phe- | II-17 |
| -PheL-Z-Phe-Z-PheL- | II-18 |
| -PheL-Z-PheL-Z-Phe- | II-19 |
| -PheL-Z-PheL-Z-PheL- | II-20 |
| -Phe-Z-PheL-Z-Cyc- | II-21 |
| -Phe-Z-Cyc-Z-PheL- | II-22 |
| -Cyc-Z-Phe-Z-PheL- | II-23 |
| -PheL-Z-Cyc-Z-PheL- | II-24 |
| -PheL-Z-PheL-Z-Cyc- | II-25 |
| -PheL-Z-Cyc-Z-Cyc- | II-26 |
| -Cyc-Z-PheL-Z-Cyc- | II-27 |

Monocyclic and bicyclic mesogenic groups $MG^1$ and bicyclic and tricyclic mesogenic groups $MG^2$ are preferred.

Further preferred are compounds of formula Ic and Id wherein $MG^2$ is selected from the formulae II-7, II-8, II-9 or II-16 to II-27, and L is F, Cl, CH$_3$, OCH$_3$, OCF$_3$ or CN.

In these preferred groups Z has the meaning given in formula I described above. Preferably Z is —COO—, —OCO—, —CH$_2$CH$_2$— —CH=CH—COO— or a single bond.

L is preferably F, Cl, CN, NO$_2$, CH$_3$, C$_2$H$_5$, OCH$_3$, OC$_2$H$_5$, COCH$_3$, COC$_2$H$_5$, CF$_3$, OCF$_3$, OCHF$_2$, OC$_2$F$_5$, in particular F, Cl, CN, CH$_3$, C$_2$H$_5$, OCH$_3$, COCH$_3$ and OCF$_3$, most preferably F, CH$_3$, OCH$_3$ and COCH$_3$.

Particularly preferred are chiral compounds wherein $MG^1$ and/or $MG^2$ are selected from the following formulae and their mirror images

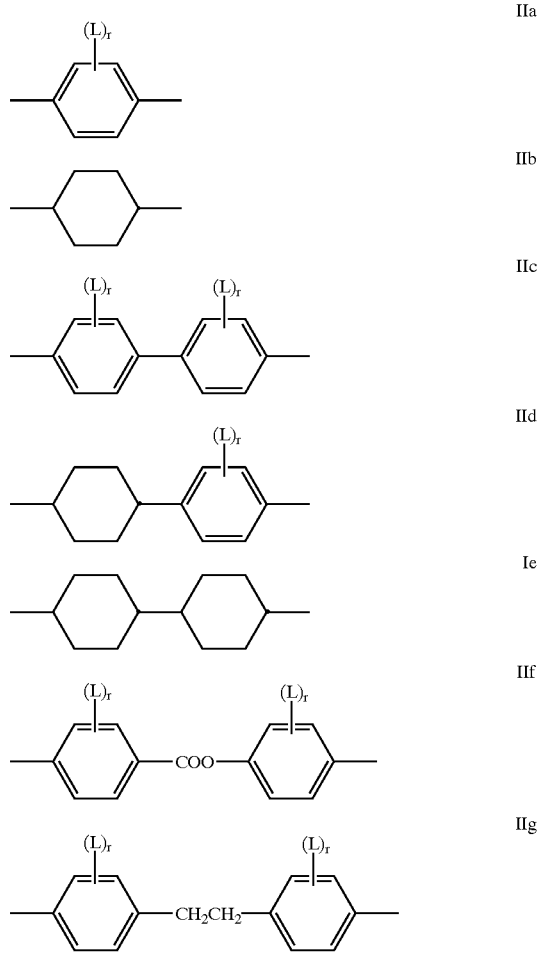

In these formulae L has the meaning given above and r is 0, 1 or 2.

The group

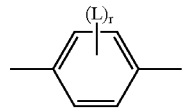

in these preferred formulae is very preferably denoting

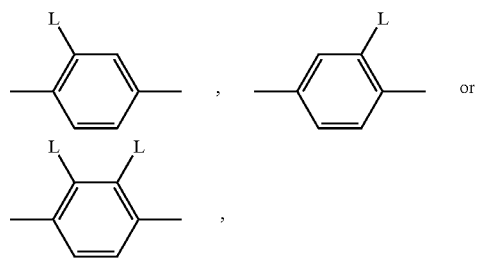

furthermore

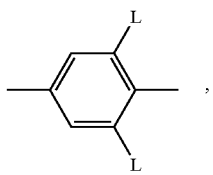

with L having each independently one of the meanings given above.

Of the compounds of formula Id especially preferred are those wherein $MG^2$ is selected according to formula IIa, IIb, IIe, IIf or IIg.

Of the compounds of formula Ig especially preferred are those wherein $MG^2$ is selected according to formula IIb, IId, IIe, IIf or IIg, furthermore those wherein $MG^2$ is selected of formula IIa and IIc and Y is different from a single bond.

$R^1$ and $R^2$ in the preferred compounds described above are particularly preferably CN, F, Cl, $OCF_3$ or an alkyl or alkoxy group with 1 to 12 C atoms. Straight-chain alkyl or alkoxy groups are especially preferred.

If $R^1$ and $R^2$ are an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8-9-oxadecyl, for example.

In the chiral compounds of formula I $R^1$ and $R^2$ may be an achiral or a chiral group. In case of a chiral group they are preferably selected according to the following formula III:

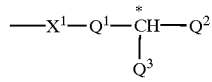

wherein $X^1$ is —O—, —S—, —CO—, —COO—, —OCO—, —OCOO— or a single bond, $Q^1$ is an alkylene or alkylene-oxy group with 1 to 10 C atoms or a single bond, $Q^2$ is an alkyl or alkoxy group with 1 to 10 C atoms which may be unsubstituted, mono- or polysubstituted by halogen or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another, $Q^3$ is halogen, a cyano group or an alkyl or alkoxy group with 1 to 4 C atoms different from $Q^2$.

Preferred chiral groups $R^1$ and $R^2$ are 2-butyl (=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-3-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy for example.

In addition, chiral compounds of the formula I containing an achiral branched group $R^1$ or $R^2$ may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

A particularly preferred embodiment of the present invention is related to polymerizable compounds of formula I and formula Ia to Ii, wherein at least one of the groups $R^1$ and/or $R^2$ is denoting P-(Sp-X)$_n$-, with Sp and X having the meanings of formula I, n being 0 or 1 and P being a polymerizable functional group.

Particularly preferred are compounds of formula Ia to Ii above wherein all of the groups $R^1$ or all of the groups $R^2$, in each case independently of one another, are denoting P-(Sp-X)$_n$-, furthermore compounds of formula Ie to Ii wherein all of the groups $R^1$ and $R^2$, in each case independently of each other, are denoting P-(Sp-X)$_n$-.

Of these polymerizable chiral compounds, especially preferred are those of the following formulae

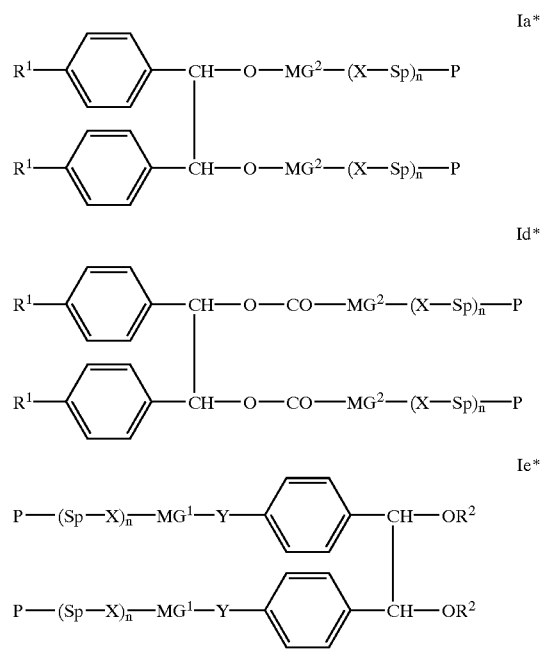

-continued

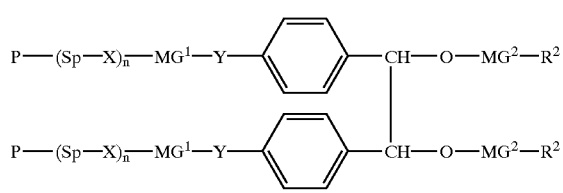

If*

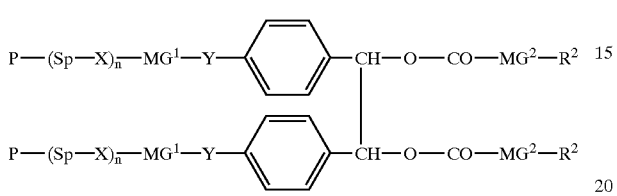

Ig* wherein $R^1$, $R^2$, $MG^1$, $MG^2$, X, Y, P, Sp and n have the meaning of formula I.

Of these preferred compounds, particularly preferred are those of formula Ia*, Id* and Ie*.

Further preferred are compounds wherein $R^1$ is H, compounds wherein n is 1, and compounds wherein one or two groups $R^1$ or $R^2$ are denoting P-(Sp-X)$_n$-.

P in formula I is preferably being selected of the following formulae

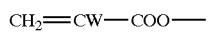 P1

 P2

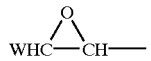 P3

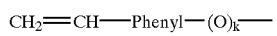 P4 with W being H, $CH_3$ or Cl and k being 0 or 1.

P is preferably a vinyl group, an acrylate group, a methacrylate group, a propenyl ether group or an epoxy group, especially preferably an acrylate or a methacrylate group.

Of the preferred compounds described above in particular preferred are those wherein n is 1.

Further preferred are compounds comprising groups $R^1$ and/or $R^2$ denoting P-(Sp-X)$_n$- wherein n is 0 and groups $R^1$ and/or $R^2$ denoting P-(Sp-X)$_n$- wherein n is 1.

In the event that two or more groups $R^1$ or $R^2$ are denoting P-Sp-X-, the spacer groups Sp may be identical or different.

As for the spacer group Sp in formula I all groups can be used that are known for this purpose to the skilled in the art. The spacer group Sp is preferably a linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)—, —CH(CN)—, —CH=CH— or —C≡C—.

Typical spacer groups are for example —($CH_2$)$_o$—, —($CH_2CH_2O$)$_r$—$CH_2CH_2$—, —$CH_2CH_2$—S—$CH_2CH_2$— or —$CH_2CH_2$—NH—$CH_2CH_2$—, with o being an integer from 2 to 12 and r being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Especially preferred are inventive chiral compounds of formula I wherein Sp is denoting an alkyl or alkoxy group with 2 to 6 C atoms. Straight-chain alkyl or alkoxy groups are especially preferred.

In another preferred embodiment of the invention the chiral compounds of formula I comprise at least one spacer group Sp that is a chiral group of the formula IV:

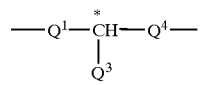

IV wherein $Q^1$ and $Q^3$ have the meanings given in formula III, and $Q^4$ is an alkylene or alkylene-oxy group with 1 to 10 C atoms or a single bond, being different from $Q^1$.

In the preferred compounds of formula If to Ii $R^1$ and $R^2$ as well as $MG^1$ and $MG^2$ on both sides of the hydrobenzoin group can be identical or different. Particularly preferred are the compounds of formula If to Ii wherein $R^1$ and $R^2$ as well as $MG^1$ and $MG^2$ are identical.

The inventive chiral compounds can be synthesized according to or in analogy to reaction scheme 1.

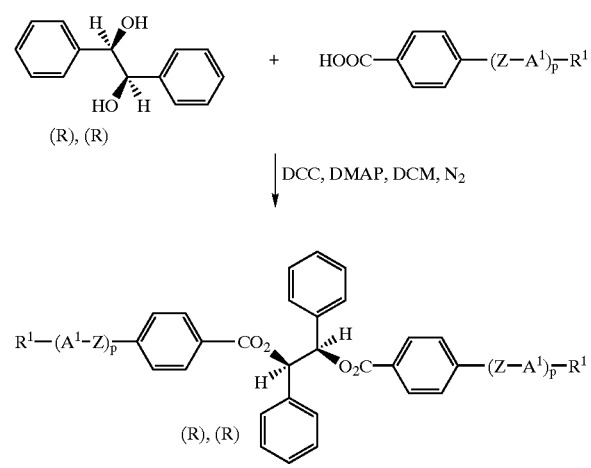

Scheme 1

In particular, polymerizable compounds of formula I can be prepared via the intermediate compound (A) according to or in analogy to reaction scheme 2.

Scheme 2

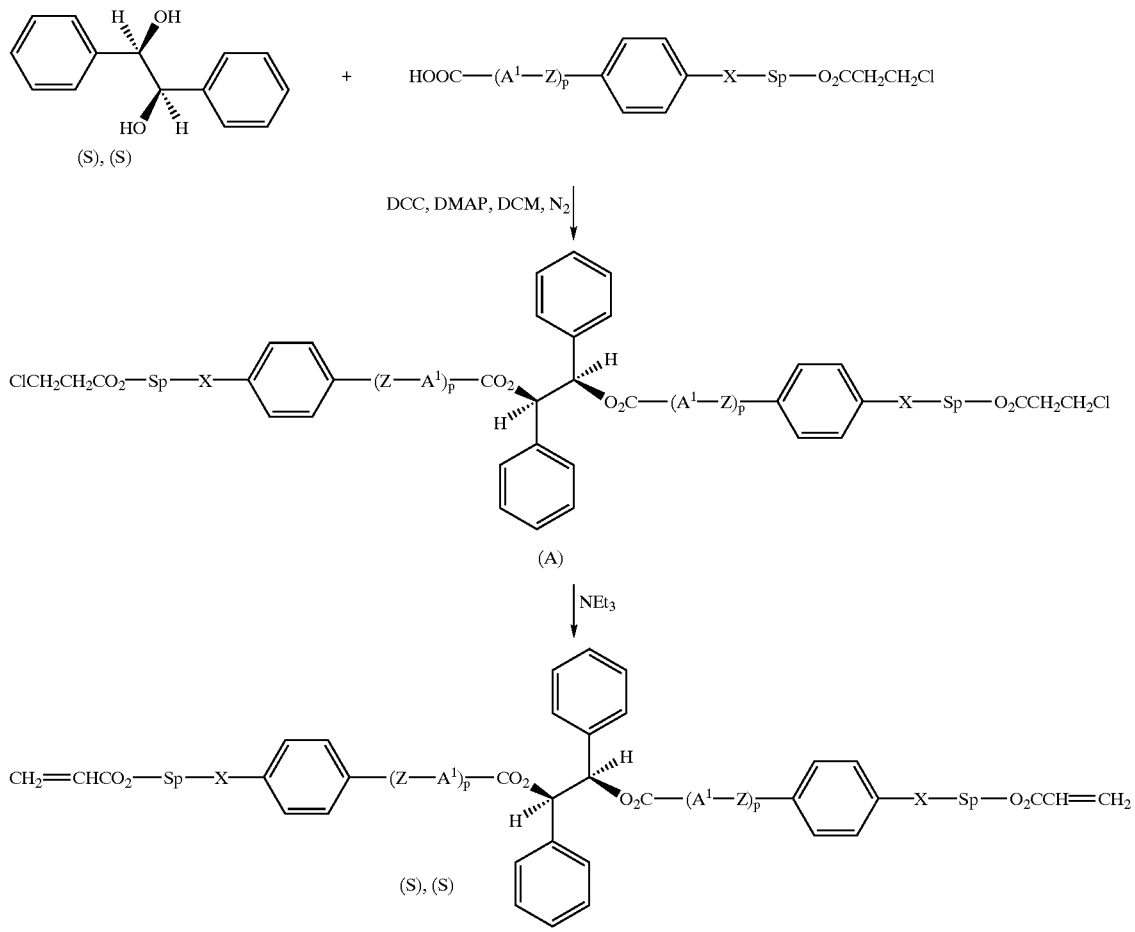

In Scheme 1 and 2 Sp, X and $R^1$ have each independently one of the meanings of formula 1, $A^1$ and Z have each independently one of the meanings given in formula II, p is an integer from 0 to 3, DCC is denoting dicyclohexylcarbodiimide, DMAP is N,N-dimethylamino-pyridine, and DCM is dichloromethane.

Other methods of synthesis can be taken from the examples.

The chiral hydrobenzoin structure element can be obtained as described e.g. by Z.-M- Wang and K. B. Sharpless, J. Org. Chem. 59, 8302, 1994. According to this method both the 1R, 2R-derivative and the 1S, 2S-derivative can be synthesized from trans-stilbene as an easily available starting material as follows

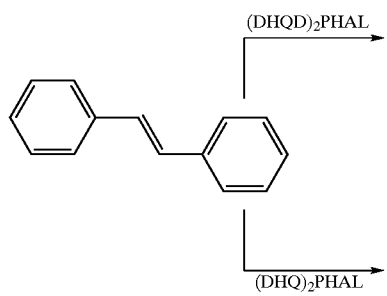

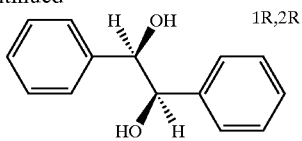

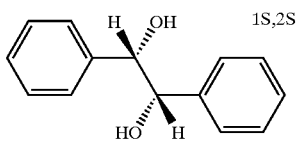

(DHQ[D])$_2$PHAL=hydroquin[id]ine-1,4-phthalazinediyl-diether (commercially available from Aldrich)

In particular preferred are chiral compounds of formula I wherein the two chiral C atoms of the hydrobenzoin group exhibit a 1R,2R- or a 1S,2S-configuration.

The inventive chiral compounds can be used in a liquid crystal mixture for displays exhibiting a twisted molecular structure of the liquid crystal matrix like, for example, supertwisted or active matrix liquid crystal displays, or in displays comprising a liquid crystal mixture with a chiral liquid crystalline phase, like for example chiral smectic or chiral nematic (cholesteric) mixtures for ferroelectric displays or cholesteric displays.

Thus, another object of the invention is a liquid crystalline mixture comprising at least one chiral compound of formula I.

Yet another object of the invention are cholesteric liquid crystal displays comprising cholesteric liquid crystalline media containing at least one chiral compound of formula I.

The inventive chiral compounds of formula I exhibit high values of the HTP. Thus liquid crystalline mixtures with a high helical twist, i.e. a short cholesteric pitch, can be prepared by using the inventive compounds, or otherwise a liquid crystalline mixture with a moderate helical twist can be achieved already when using the inventive compounds as dopants in low amounts.

The high HTP values of the inventive compounds makes them also suitable to be used in combination with other compounds for the temperature compensation of the properties of liquid crystal mixtures, such as the cholesteric pitch, and of the properties of displays, e.g. such as the threshold voltage.

In a preferred embodiment of the invention the chiral compounds show a strong temperature dependence of the HTP in nematic liquid crystal mixtures.

The inventive compounds are furthermore advantageous because they are affecting the physical properties of the liquid crystalline mixture only to a minor extent.

Thus, when admixing the chiral compounds of formula I for example to a liquid crystalline mixture with positive dielectric anisotropy that is used in a liquid crystal display, $\Delta\epsilon$ is being only slightly reduced and the viscosity of the liquid crystalline mixture is increased only to a small extent. This leads to lower voltages and improved switching times of the display when compared to a display comprising conventional dopants.

In a particularly preferred embodiment of the invention the chiral compounds show a small temperature dependence of the HTP in nematic liquid crystal mixtures.

The liquid crystalline mixture according to the invention comprises preferably 0.001 to 15%, in particular 0.01 to 8% and very particularly preferably 0.1 to 5% by weight of chiral compounds of formula I.

The liquid crystalline mixture according to the invention preferably comprises 1 to 3 chiral compounds of formula I.

For temperature compensation applications as described above the liquid crystalline mixture preferably contains a chiral component which contains at least one chiral compound of formula I.

In a preferred embodiment of the invention the liquid crystalline mixture is consisting of 2 to 25, preferably 3 to 15 compounds, at least one of which is a chiral compound of formula I. The other compounds are preferably low molecular weight liquid crystalline compounds selected from nematic or nematogenic substances, for example from the known classes of the azoxybenzenes, benzylideneanilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexyl-biphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl-2-cyclohexyl-phenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystalline mixture of this preferred embodiment is based on the achiral compounds of this type.

The most important compounds that are possible as components of these liquid crystalline mixtures can be characterized by the following formula

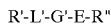

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$—, —CO—O—, —CH$_2$—O—, —CO—S—, —CH$_2$—S—, —CH=N—, —COO—Phe—COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

The inventive compounds are in particular useful for anisotropic polymer gels and for low molar mass or polymerizable or polymerized cholesteric liquid crystalline mixtures for cholesteric displays, such as for example phase change displays or surface stabilized or polymer stabilized cholesteric texture displays (SSCT, PSCT).

A further advantage of the chiral compounds according to the invention is that cholesteric liquid crystalline mixtures or materials comprising these compounds exhibit a low temperature dependence of the reflection wavelength $d\lambda/dT$ (T=temperature, $\lambda$=reflection wavelength maximum).

Cholesteric displays are described for example in WO 92/19695, WO 93/23496, U.S. Pat. No. 5,453,863 or U.S. Pat. No. 5,493,430, with the entire disclosure of these documents being introduced into this application by way of reference.

Furthermore, anisotropic polymer gels and displays comprising them are disclosed for example in DE 195 04 224 and GB 2 279 659.

It has been found that PSCT displays comprising the inventive compounds have reduced response times, lower voltages and improved contrast compared to displays comprising conventional dopants, like e.g. R 811 or CB 15, that are commercially available by Merck KGaA (Darmstadt, Germany). For example, a PSCT display in which a conventional dopant was replaced by a chiral compound according to the invention showed a reduction of the switching time of up to 50%.

A cholesteric film made by using the inventive compounds unexpectedly showed improved brightness, leading to a better contrast between the colored planar texture and the almost clear focal conic state which is made black using a black backplate.

The inventive chiral compounds and polymerizable liquid crystalline mixtures comprising these compounds are also particularly useful for the preparation of anisotropic polymer films with a chiral liquid crystalline phase such as cholesteric or chiral smectic polymer films, that preferably exhibit a chiral liquid crystalline phase having uniform orientation.

Examples of oriented cholesteric polymer films used as broad waveband polarizers can be found in EP 0 606 940, whereas I. Heynderickx and D. J. Broer in Mol.Cryst.Liq.Cryst. 203,113–126 (1991) describe crosslinked cholesteric polymer films that are made of liquid crystalline diacrylates and contain a low molecular weight chiral dopant. EP 0 562 681 A1 discloses polymer networks with a smectic structure that contains chiral low molar mass compounds and exhibits a piezoelectric effect.

It has been found that cholesteric polymer films made by using the inventive chiral compounds are brighter compared to films comprising dopants of prior art like e.g. R 811 or CB 15 as mentioned above.

For the preparation of anisotropic polymer gels or oriented polymer films, the liquid crystalline mixture should comprise at least one polymerizable compound, preferably a polymerizable mesogenic compound, in addition to chiral compounds of formula I.

Thus, another object of the invention is polymerizable liquid crystalline mixtures comprising at least one chiral compound of formula I and at least one polymerizable mesogenic compound.

The polymerizable mesogenic compounds are preferably selected of formula V $$P\text{-}(SP\text{-}X)_n\text{-}(A^1\text{-}Z)_m\text{-}A^2\text{-}R^5 \qquad V$$

wherein

P, Sp, X and n have the meaning of formula I, $A^1$, Z and m have the meaning of formula II, $A^2$ has one of the meanings of $A^1$, and $R^5$ has the meaning of $R^1$ in formula I.

Polymerizable mesogenic compounds according to formula V are described for example in WO 93/22397; EP 0,261,712; DE 195,04,224; DE 4,408,171 or DE 4,405,316. The compounds disclosed in these documents, however, are to be regarded merely as examples that shall not limit the scope of this invention.

Furthermore, typical examples representing polymerizable mesogenic compounds are shown in the following list of compounds, which should, however, be taken only as illustrative and is in no way intended to restrict, but instead to explain the present invention:

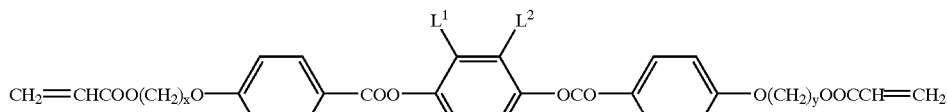
(V1)

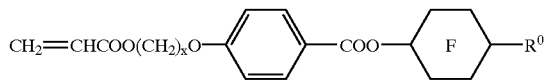
(V2)

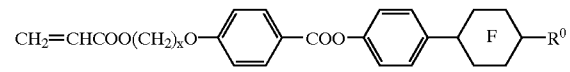
(V3)

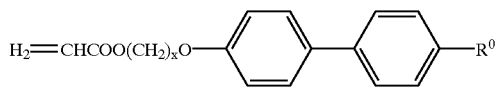
(V4)

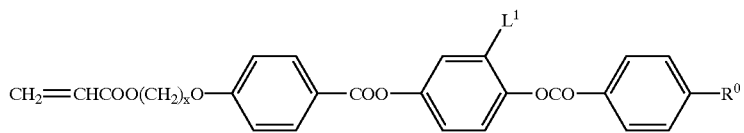
(V5)

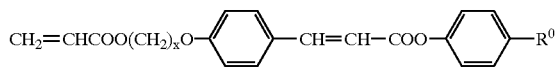
(V6)

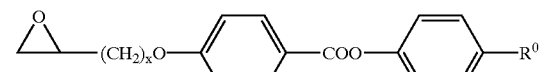
(V7)

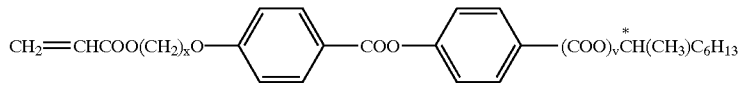
(V8)

-continued

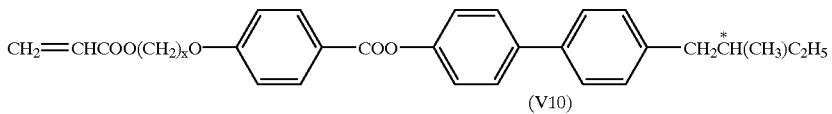
(V9)

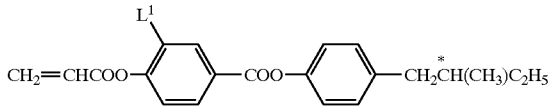
(V10)

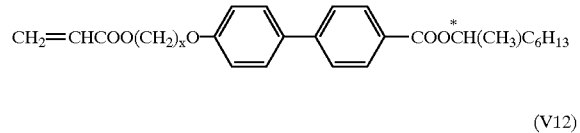
(V11)

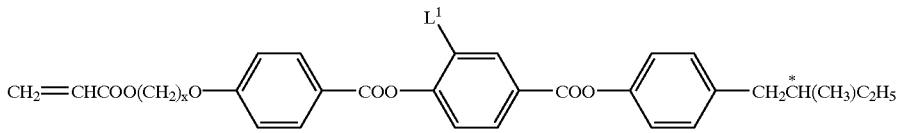
(V12)

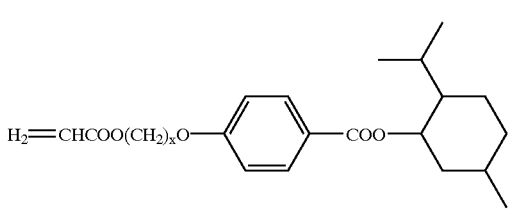
(V13)

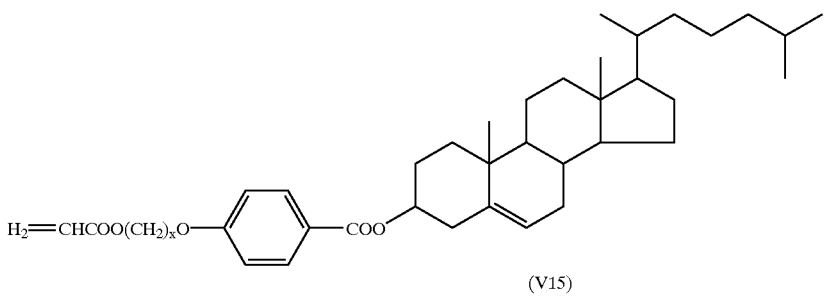
(V14)

(V15)

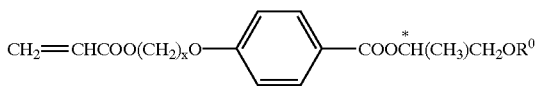

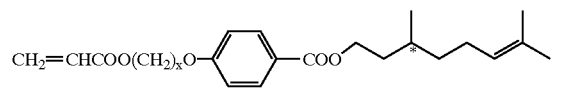
(V16)

(V17)

In these compounds x and y are each independently 1 to 12, F is a 1,4-phenylene or 1,4-cyclohexylene group, $R^0$ is halogen, cyano or an optionally halogenated alkyl or alkoxy group with 1 to 12 C atoms and $L^1$ and $L^2$ are each independently H, F, Cl, CN, or an optionally halogenated alkyl, alkoxy or alkanoyl group with 1 to 7 C atoms.

The polymerizable mesogenic compounds of formula V can be prepared by methods which are known per se and which are described in the documents cited above and, for example, in standard works of organic chemistry such as, for example, Houben-Weyl, Methoden der organischen Chemie, Thieme-Verlag, Stuttgart.

The polymerizable mesogenic compounds of formula V can be mono- or bifucntional, i.e. they can carry one or two polymerizable functional groups.

In a preferred embodiment of the invention the polymerizable liquid crystalline mixtures comprise at least one inventive chiral compound, at least one monofucntional and at least one bifunctional polymerizable compound of formula V.

In another preferred embodiment the polymerizable liquid crystalline mixtures comprise at least one inventive chiral compound and at least two monofunctional compounds of formula V.

It is also possible that the polymerizable liquid crystalline mixture comprises one or more polymerizable compounds of formula I instead of or in addition to the polymerizable mesogenic compounds of formula V.

Thus, another object of the invention is polymerizable liquid crystalline mixtures comprising at least one chiral compound of formula I comprising at least one polymerizable functional group.

In a preferred embodiment the polymerizable liquid crystalline mixtures comprise at least one chiral compound of formula I comprising one polymerizable functional group.

In another preferred embodiment the polymerizable liquid crystalline mixtures comprise at least one chiral compound of formula I comprising two polymerizable functional groups.

Another object of the invention is an anisotropic polymer film with an oriented chiral liquid crystalline phase obtainable by (co)polymerizing a liquid crystalline mixture comprising at least one chiral compound of formula I and at least one polymerizable mesogenic compound preferably selected of formula V and/or at least one polymerizable chiral compound of formula I.

To prepare anisotropic polymer film with a chiral liquid crystalline phase with uniform orientation the inventive liquid crystalline mixtures, for example, are coated onto a substrate, aligned and polymerized in situ by exposing them to heat or actinic radiation. Alignment and curing are preferably carried out in the liquid crystalline phase of the liquid crystalline mixtures.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

For example, when polymerizing by means of UV light, a photoinitiator can be used that decomposes under UV irradiation to produce free radicals or ions that start the polymerization reaction.

It is also possible to use a cationic photoinitiator, when curing reactive mesogens with for example vinyl and epoxide reactive groups, that photocures with cations instead of free radicals.

As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

Preferably the polymerizable liquid crystalline mixtures comprising polymerizable chiral compounds of formula I and/or polymerizable mesogenic compounds of formula V additionally comprise 0.01 to 10%, in particular 0.05 to 8%, very preferably 0.1 to 5% by weight of a photoinitiator, especially preferably a UV-photoinitiator.

In a preferred embodiment of the invention the polymerization of the polymerizable mesogenic material is carried out under an atmosphere of inert gas, preferably under a nitrogen atmosphere.

As a substrate for example a glass or quartz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization.

Isotropic or birefringent substrates can be used. In case the substrate is not removed from the polymerized film after polymerization, preferably isotropic substrates are used.

Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

In a preferred embodiment of the present invention, the inventive mixture of the polymerizable liquid crystalline mixture comprising a chiral compound of formula I is coated as a thin layer on a substrate or between substrate, and is preferably aligned in its chiral mesophase, e.g., the cholesteric or chiral smectic phase, to give a planar orientation, i.e. an orientation so that the axis of the molecular helix extends transversely to the layer.

A planar orientation can be achieved for example by shearing the mixture, e.g. by means of a doctor blade. It is also possible to apply an alignment layer, for example a layer of rubbed polyimide or sputtered $SiO_x$, on top of at least one of the substrates.

In another preferred embodiment, a second substrate is put on top of the coated material. In this case, the shearing caused by putting together the two substrates is sufficient to give good alignment.

It is also possible to apply an electric or magnetic field to the coated mixture.

In some cases it is of advantage to apply a second substrate not only to aid alignment of the polymerizable mixture but also to exclude oxygen that may inhibit the polymerization. Alternatively the curing can be carried out under an atmosphere of inert gas. However, curing in air is also possible using suitable photoinitiators and high lamp power. When using a cationic photoinitiator oxygen exclusion most often is not needed, but water should be excluded.

A detailed description of the in situ polymerization of polymerizable mesogenic compounds can be found in D. J. Broer et al., Makromolekulare Chemie 190, 2255 (1989).

The inventive polymerizable liquid crystalline mixtures comprise preferably 0.001 to 15%, in particular 0.01 to 8% and very particularly preferably 0.1 to 5% by weight of non-polymerizable chiral compounds of formula I.

Polymerizable liquid crystalline mixtures are preferred that comprise 1 to 3 chiral compounds of formula I.

If polymerizable chiral compounds of formula I are present in the inventive polymerizable liquid crystalline mixtures, these compounds can also be used in the inventive polymerizable liquid crystalline mixtures in higher amounts than given above for the non-polymerizable chiral compounds of formula I.

In a preferred embodiment of the present invention the polymerizable liquid crystalline mixtures are comprising 1 to 80% by weight, preferably 2 to 60%, in particular 5 to 40% by weight of a polymerizable chiral compound of formula I comprising at least one polymerizable functional group.

Of the polymerizable liquid crystalline mixtures comprising one or more polymerizable chiral compounds of formula I with one polymerizable functional group (=monofunctional compounds), particularly preferred are those comprising 1 to 60%, in particular 2 to 45%, very preferably 3 to 35% by weight of a polymerizable chiral monofunctional compound of formula I.

Of the polymerizable liquid crystalline mixtures comprising one or more polymerizable chiral compounds of formula I with two polymerizable functional groups (=bifunctional compounds), particularly preferred are those comprising 1 to 50%, in particular 2 to 35%, very preferably 3 to 25% by weight of a polymerizable chiral bifunctional compound of formula I.

The inventive polymerizable liquid crystalline mixtures can additionally comprise one or more other suitable components, such as, for example, catalysts, sensitizers, stabilizers, co-reacting monomers or surface-active compounds.

In a preferred embodiment of the invention, the inventive polymerizable liquid crystalline mixture comprises a stabilizer that is used to prevent undesired spontaneous polymerization for example during storage of the composition. As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add up to 20% of a non mesogenic compound with two or more polymerizable functional groups to the polymerizable composition alternatively or additionally to the multifunctional polymerizable mesogenic compounds.

Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystalline mixtures can be polymerized in situ as described above, however, in this case alignment of the polymerizable mixture is not necessary.

The inventive chiral compounds of formula I can also be used for the preparation of thermochromic liquid crystalline mixtures. Such mixtures are characterized in that they exhibit a chiral liquid crystalline phase or chiral mesophase, like e.g. a chiral smectic phase or a chiral nematic (=cholesteric) phase, with a helically twisted molecular structure that shows selective reflection of a specific waveband of light, wherein the pitch of the molecular helix and thereby the reflected wavelengths are depending on the temperature.

Especially preferred are inventive liquid crystalline mixtures with thermochromic behavior that exhibit a cholesteric phase. Of these preferred compositions, further preferred are compositions that exhibit a cholesteric phase and a smectic phase, most preferably a chiral smectic phase, at temperatures below the temperature range of the cholesteric phase. The inventive liquid crystalline mixtures exhibiting thermochromic behavior can be polymerizable or non-polymerizable.

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

The entire disclosure of all applications, patents and publications, cited above and below, and of corresponding European Application No. 97 113 935.7, filed Aug. 13, 1997 is hereby incorporated by reference.

The preceding examples can be repeated with similar success by substituting the generically or specifically described reactants and/or operating conditions of this invention for those used in the preceding examples.

In the foregoing and in the following examples, unless otherwise indicated, all temperatures are set forth uncorrected in degrees Celsius and all parts and percentages are by weight.

The values of the helical twisting power HTP of a chiral compound in a liquid crystalline host are given according to the equation HTP=$(p \cdot c)^{-1}$ in $\mu m^{-1}$, wherein p is the pitch of the molecular helix, given in $\mu m$, and c is the concentration by weight of the chiral compound in the host given in relative values (thus, e.g. a concentration of 1% by weight is corresponding to a value of c of 0.01).

The following abbreviations are used to illustrate the liquid crystalline phase behaviour of the compounds: K=crystalline; N=nematic; S=smectic; Ch=cholesteric; I=isotropic. The numbers between these symbols indicate the phase transition temperatures in degree Celsius.

In addition, the following abbreviations are used
DCC=dicyclohexylcarbodiimide
DCU=dicyclohexylurea
DMAP=N,N-dimethylaminopyridine
DCM=dichloromethane
HTP=helical twisting power

EXAMPLE 1

The compound (1) was prepared according to reaction scheme 1 (with $R^1$-$(A^1$-$Z)_p$- in scheme denoting

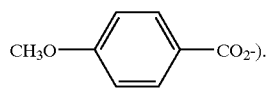

(1)

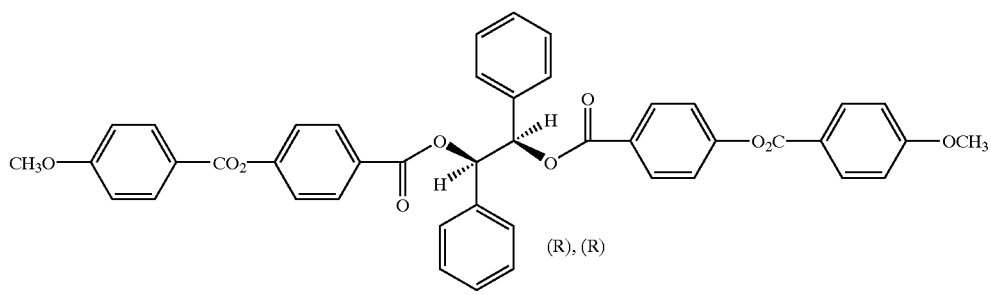

Compound (1) exhibits a HTP of 43 $\mu m^{-1}$, being determined in the nematic host mixture E63. The host mixture E63 which is commercially available under the name BL004 from Merck Ltd., Poole, UK and exhibits the following properties

| | |
|---|---|
| clearing point | 78.5° C. |
| birefringence | 0.224 |
| dielectric anisotropy | +14.6 |
| viscosity (at 20° C.) | 38 mm²/s |

As known in the art, E63 comprises (4-alkyl-4'-cyano) biphenyls, (4-alkyl-4'- cyano)cycloalkylphenyls, (4-alkyl-4'-cyano)terphenyls, (4-alkyl-4'-cyano)cyclohexylbiphenyls and (4-alkyl-4'-cyano)biphenyl carboxylic acid biphenyl esters.

EXAMPLE 2

The compound (2) was prepared according to reaction scheme 2 (with p being 0 and -Sp-X- being —(CH$_2$)$_4$—O—) as follows.

(S),(S)-(−)-1,2-Diphenyl-1,2-ethanediol (23.2 mmol), DCC (48.7 mmol), 4-(3-chloropropionylhexyloxy)benzoic acid (46.4 mmol) and a catalytic amount of DMAP were stirred in dichloromethane at room temperature under an atmosphere of nitrogen for 48 hours. DCU was removed by filtration. The filtrate was washed with water, dried with Na$_2$SO$_4$ and evaporated to dryness on a rotatory evaporator. The crude material was purified by flash column chromatography (eluant=DCM). Evaporation of appropriate fractions yielded (A) as a pale green colored, sticky oil. Yield= 4.6 mmol (20%).

(A) (4.4 mmol), triethylamine (6 equivalents) and DCM (20 ml) were stirred at 35° C. for 24 hours. The chlorinated solution was washed with water and dried over MgSO$_4$, then evaporated to dryness leaving compound (2) as a waxy solid. Yield=4.3 mmol (98%).

Compound (2) exhibits a melting point of 55° C. The HTP of compound (2) is 12 $\mu m^{-1}$, determined at a concentration of 4.1% by weight in the nematic host mixture E63.

EXAMPLE 3

The compound (3) was prepared according to reaction scheme 2 (with (A$^1$-Z)$_p$- denoting

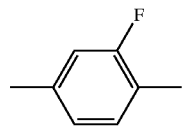

and -Sp-X- being (CH$_2$)$_4$—O—) as follows.

(R),(R)-(+)-1,2-Diphenyl-1,2-ethanediol (3.2 g, 15 mmol), DCC (30 mmol), 4-(3-chloropropionylbutyloxy) benzoic acid (11.3 g, 30 mmol) and a catalytic amount of DMAP were stirred in dichloromethane at room temperature under an atmosphere of nitrogen for 36 hours. DCU was removed by filtration and the filtrate was evaporated to dryness. The crude material was purified by flash column chromatography (eluant=DCM) to yield (A3). Yield=1.2 mmol (8%).

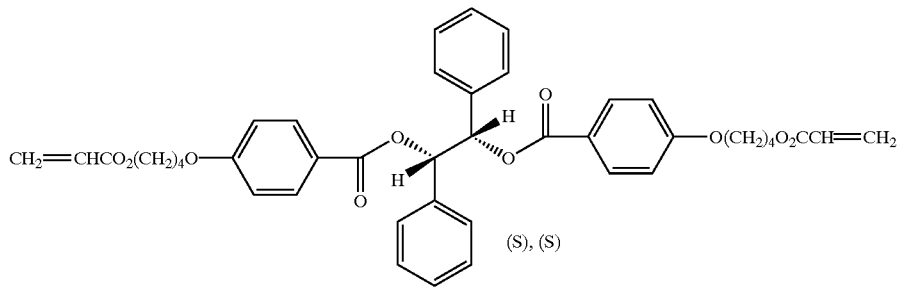

(2)

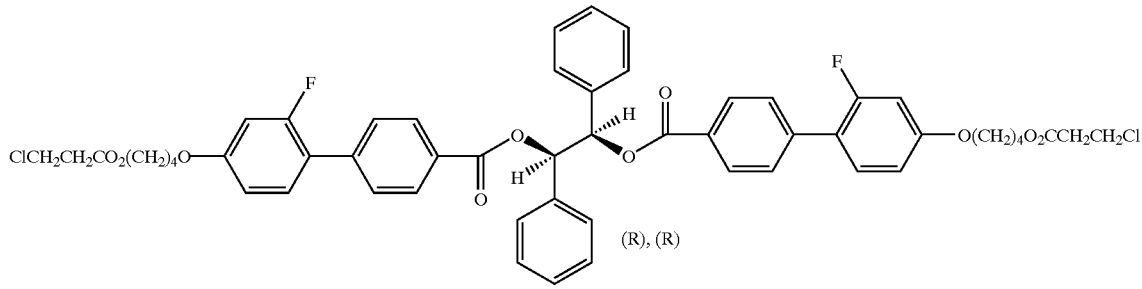
(A3)

(A3) (1.1 mmol), triethylamine (6 equivalents) and dichloromethane (20 ml) were stirred at 35° C. for 24 hours. The solution was evaporated to dryness to give compound (3) as a sticky oil. Yield=0.9 mmol (83%).

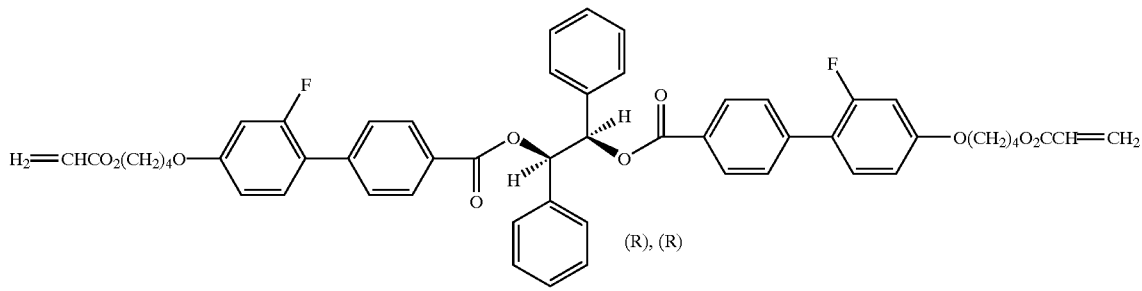
(3)

The HTP of compound (3) is 31 $\mu m^{-1}$, determined at a concentration of 6.1% by weight in the nematic host mixture E63.

EXAMPLE 4

The following compounds have been prepared according to or in analogy to reaction scheme 1. The HTP of these compounds has been determined in the nematic host mixture E63.

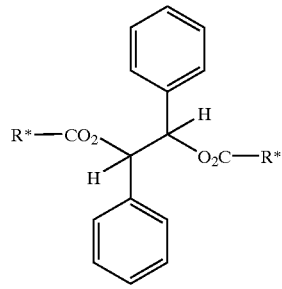

| No. | R* | config.[1] | m.p.(° C.)[2] | HTP($\mu m^{-1}$) |
|---|---|---|---|---|
| 4a | C$_7$H$_{15}$—⟨cyclohexyl⟩—⟨phenyl⟩— | (R, R) | 138 | 49 |

-continued
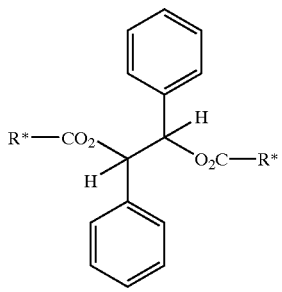
| No. | R* | config.[1] | m.p.(° C.)[2] | HTP(μm⁻¹) |
|---|---|---|---|---|
| 4b | C₃H₇—⟨H⟩—⟨⟩—(CH₂)₄O— | (R, R) | 94 | 4 |
| 4c | C₃H₇—⟨⟩—CH₂— | (R, R) | 112 | 2 |
| 4d | C₇H₁₅—⟨H⟩—⟨⟩— | (S, S) | 138 | 45 |
| 4e | C₅H₁₁—⟨H⟩—⟨H⟩— | (S, S) | 137 | 45 |
| 4f | C₇H₁₅—⟨⟩—⟨⟩— | (S, S) | 167 | 45 |
| 4g | C₅H₁₁—⟨⟩(F)—⟨⟩— | (S, S) | 120 | 45 |
| 4h | C₈H₁₇O—⟨⟩—⟨⟩(F,F)— | (S, S) | 67 | 57 |
| 4i | C₃H₇—⟨H⟩—CH₂CH₂—⟨⟩(F,F)— | (S, S) | 128 | 16 |
| 4k | C₃H₇—⟨H⟩—CH₂CH₂—⟨⟩— | (S, S) | 138 | 56 |

-continued

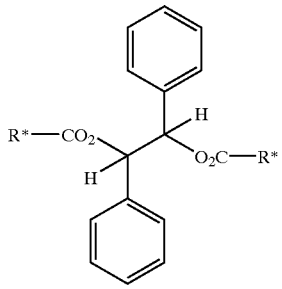

| No. | R* | config.[1] | m.p.(° C.)[2] | HTP($\mu m^{-1}$) |
|---|---|---|---|---|
| 41 | 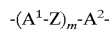 | (S, S) | 153 | 46 |

[1] config. = stereoconfiguration of the hydrobenzoin group
[2] m.p. = melting point The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

What is claimed is:

1. A chiral compound of formula I

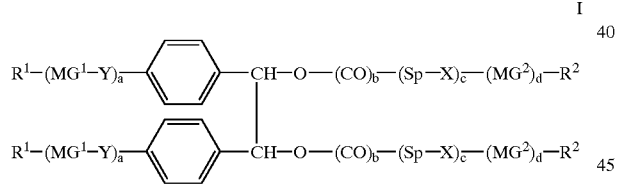

wherein

Sp in each case independently denotes a spacer group with up to 20 C atoms,

X in each case independently denotes —O—, —S—, —CO—, —COO—, —OCO—, —OCO—O—, —CO—NH—, —NH—CO—, —OCH$_2$—, —CH$_2$O—, —SCH$_2$—, —CH$_2$S— or a single bond, Y in each case independently denotes —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond, a, b, c and d are in each case independently 0 or 1, provided that each a and d are not 0 at the same time, and provided that when a is 1, $R^1$ is not hydrogen, $R^1$ and $R^2$ are independently of each other H, CN, halogen or a straight-chain or branched alkyl radical with 1 to 25 C atoms which is unsubstituted, mono- or polysubstituted by halogen or CN, optionally one or more non-adjacent CH$_2$ groups being replaced, in each case independently from one another, by —O—, —S—, —NH—, —N(CH$_3$)—, —CO—, —COO—, —OCO—, —OCO—O, —S—CO—, —CO—S— or —C≡C— in such a manner that oxygen atoms are not linked directly to one another, or alternatively $R^1$ and $R^2$ denotes P-(Sp-X)$_n$-, with Sp and X having the meanings given above, n being 0 or 1 and P being a polymerizable group, and $MG^1$ and $MG^2$ are each independently a mesogenic or mesogenity supporting group of formula II $$-(A^1-Z)_m-A^2-\qquad\qquad II$$

with z denoting —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond, $A^1$ and $A^2$ being in each case independently 1,4-phenylene in which, in addition, one or more CH groups are optionally replaced by N; 1,4-cyclohexylene in which, in addition, one or two non-adjacent CH$_2$ groups are optionally replaced by O and/or S; 1,4-cyclohexenylene; 1,4-bicyclo-(2,2,2)-octylene; piperidine-1,4-diyl; naphthalene-2,6-diyl; decahydronaphthalene-2,6-diyl; or 1,2,3,4-tetrahydronaphthalene-2,6-diyl; all these groups optionally, being unsubstituted, mono- or polysubstituted with F or Cl, cyano or nitro groups or alkyl, alkoxy or alkanoyl groups having 1 to 7 C atoms optionally wherein one or more H atoms thereon are replaced by F or Cl, and m being 0, 1, 2 or 3;

provided that, wherein a=c=0 and b=d=1, $MG^2$ is selected from groups of the following formulae II-1 to II-10 and II-12 to II-24 or their mirror images:

| | |
|---|---|
| -Phe- | II-1 |
| -Cyc- | II-2 |
| -PheL- | II-3 |
| -Phe-Z-Phe- | II-4 |
| -Phe-Z-Cyc- | II-5 |
| -Cyc-Z-Cyc- | II-6 |
| -PheL-Z-Phe- | II-7 |
| -PheL-Z-Cyc- | II-8 |
| -PheL-Z-PheL- | II-9 |
| -Phe-Z-Phe-Z-Phe- | II-10 |
| -Phe-Z-Cyc-Z-Phe- | II-12 |
| -Cyc-Z-Phe-Z-Cyc- | II-13 |
| -Phe-Z-Cyc-Z-Cyc- | II-14 |
| -Cyc-Z-Cyc-Z-Cyc- | II-15 |
| -Phe-Z-Phe-Z-PheL- | II-16 |
| -Phe-Z-PheL-Z-Phe- | II-17 |
| -PheL-Z-Phe-Z-PheL- | II-18 |
| -PheL-Z-PheL-Z-Phe- | II-19 |
| -PheL-Z-PheL-Z-PheL- | II-20 |
| -Phe-Z-PheL-Z-Cyc- | II-21 |
| -Phe-Z-Cyc-Z-PheL- | II-22 |
| -Cyc-Z-Phe-Z-PheL- | II-23 |
| -PheL-Z-Cyc-Z-PheL- | II-24 |
| -PheL-Z-PheL-Z-Cyc- | II-25 |
| -PheL-Z-Cyc-Z-Cyc- | II-26 |
| -Cyc-Z-PheL-Z-Cyc- | II-27 | where Phe in these groups is 1,4-phenylene, PheL is a 1,4-phenylene group which is substituted by at least one group L, with L being F, Cl, CN or an optionally flourinated alkyl, alkoxy or alkanoyl group with 1 to 4 C atoms, and Cyc is 1,4-cyclohxylene, and further provided: that when a, b, and c are 0 and, d is 1 and $MG^2$ is unsubstituted 1,4-phenylene or 1,4-cyclohexylene, then $R^2$ is not hydrogen; than when a=c=0, b=d=1 and $MG^2$ is Phe, then $R^2$ is not Br or $OCH_3$; and that when a=c=0, b=d=1 and $MG^2$ is of formula II-4 of II-5, then Z is —COO—, —OCO—, —$CH_2CH_2$— or —CH═CH—COO.

2. A chiral compound according to claim 1, selected from the compounds of the following formulae:

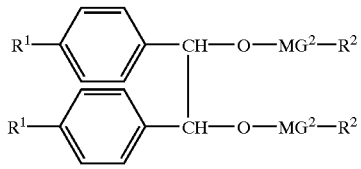
Ia

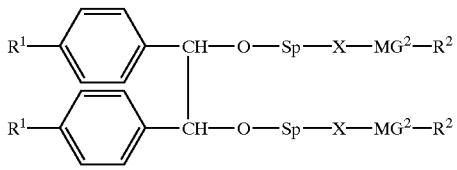
Ib

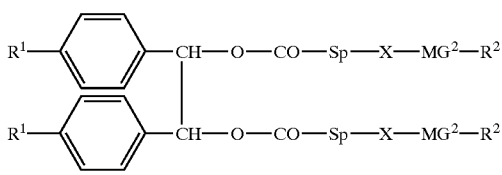
Ic

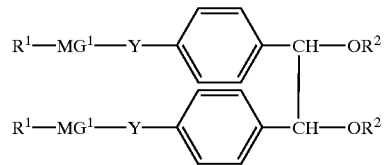
Ie

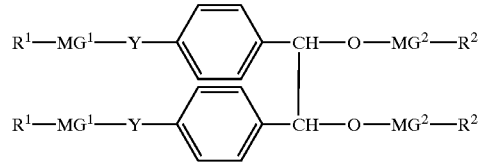
If

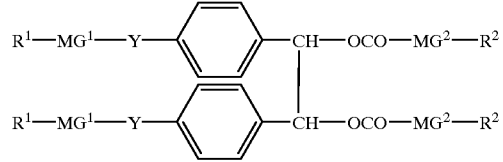
Ig wherein $R^1$, $R^2$, $MG^1$, $MG^2$, Sp, X and Y have the meaning given for formula I.

3. A chiral compound according to claim 1, wherein at least one of $R^1$ and $R^2$ is P-(Sp-X)$_n$-.

4. A chiral compound according to claim 3, wherein both groups $R^1$ and/or both groups $R^2$ are P-(SP-X)$_n$-.

5. A chiral compound according to claim 1, wherein at least one of groups $R^1$ and $R^2$ is alkyl or alkoxy with 1 to 12 C atoms.

6. A chiral compound according to claim 1, wherein $MG^1$ and $MG^2$ are independently selected from groups of the following formulae

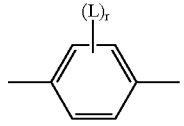
IIa

IIb

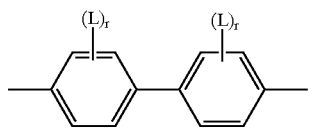
IIc

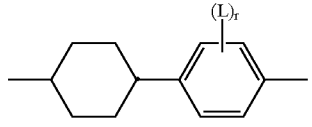
IId

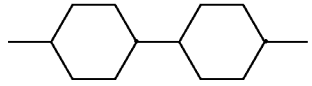
Ie

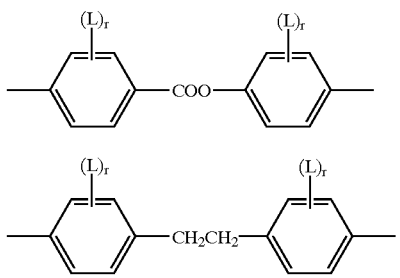

wherein L in each case independently denotes halogen, a cyano or nitro group or an alkyl, alkoxy or alkanoyl group having 1 to 7 C atoms wherein one or more H atoms are optionally substituted by F or Cl and r is 0, 1 or 2.

7. A liquid crystalline mixture comprising at least one chiral compound according to claim 1.

8. A polymerizable liquid crystalline mixture comprising at least one chiral compound according to formula I of claim 1 and at least one polymerizable mesogenic compound having at least one polymerizable functional group which is not of the formula I.

9. A liquid crystalline mixture comprising 0.001 to 15% by weight of at least one non-polymerizable chiral compound according to claim 1.

10. A polymerizable liquid crystalline mixture comprising 0.001 to 15% by weight of at least one non-polymerizable chiral compound according to claim 1 and at least one polymerizable mesogenic compound having at least one polymerizable functional group.

11. A liquid crystalline mixture comprising 1 to 80% by weight of at least one polymerizable chiral compound according to claim 1.

12. An anisotropic polymer film with a chiral liquid crystalline phase comprising at least one chiral compound according to claim 1.

13. A polymer film with a chiral liquid crystalline phase obtained by (co)polymerizing a liquid crystalline mixture according to claim 8.

14. An active or passive optical element which comprises, as dielectric, a liquid crystalline mixture according to claim 7.

15. A liquid crystal display which comprises a liquid crystalline mixture according to claim 7.

16. The liquid crystal display of claim 15, which is a surface stabilized or polymer stabilized cholesteric texture display.

17. A chiral compound of formula I

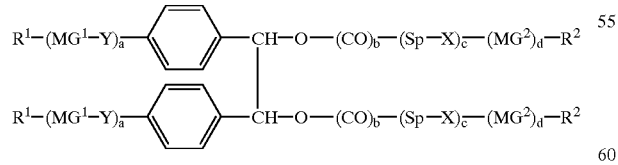

wherein
Sp in each case independently denotes a spacer group with up to 20 C atoms, —OCO—O—, —CO—NH—, —NH—CO—, —OCH$_2$—, —CH$_2$O—, —SCH$_2$—, —CH$_2$S— or a single bond, in each case independently denotes —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C— or a single bond, a, b, c, and d are in each case independently 0 or 1, provided that each a and d are not 0 at the same time, R$_1$ and R$_2$ are independently of each other H, CN, halogen or a straight-chain or branched alkyl radical with 1 to 25 C atoms which is unsubsituted, mono- or polysubstituted by halogen or CN, optionally one or more non-adjacent CH$_2$ groups being replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or alternatively R$^1$ and R$^2$ denotes P-(Sp-X)$_n$-, with Sp and X having the meanings given above, n being 0 or 1 and P being a polymerizable group; provided that at least one of R$^1$ and R$^2$ is a P-(Sp-X)$_n$- group, and MG$^1$ and MG$^2$ are each independently a mesogenic or mesogenity supporting group of formula II $$-(A^1-Z)_m-A^2-$$    II with
Z denoting —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—, —CH=CH—, —C≡C— or a single bond, A$^1$ and A$^2$ being in each case independently 1,4-phenylene in which, in addition, one or more CH groups are optionally replaced by N; 1,4-cyclohexylene in which, in addition, one or two non-adacent Ch$_2$ groups are optionally replaced by O and/or S; 1,4-cyclohexenylene; 1,4-bicyclo-(2,2,2)-octylene; piperidine-1,4-diyl; naphthalene-2,6-diyl; decahydronaphthalene-2,6-diyl; or 1,2,3,4-tetrahydronaphthalene-2,6-diyl; all these groups optionally being unsubstituted, mono- or polysubstituted with halogen, cyano or nitro groups or alkyl, alkoxy or alkanoyl groups having 1 to 7 C atoms optionally wherein one or more H atoms thereon are replaced by F or Cl , and m being 0, 1, 2 or 3.

18. A chiral compound according to claim 17, selected from the compounds of the following formulea:

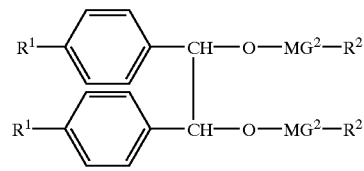

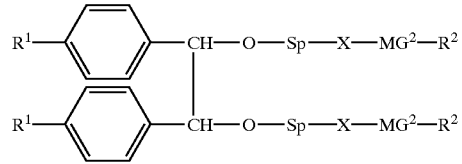

-continued

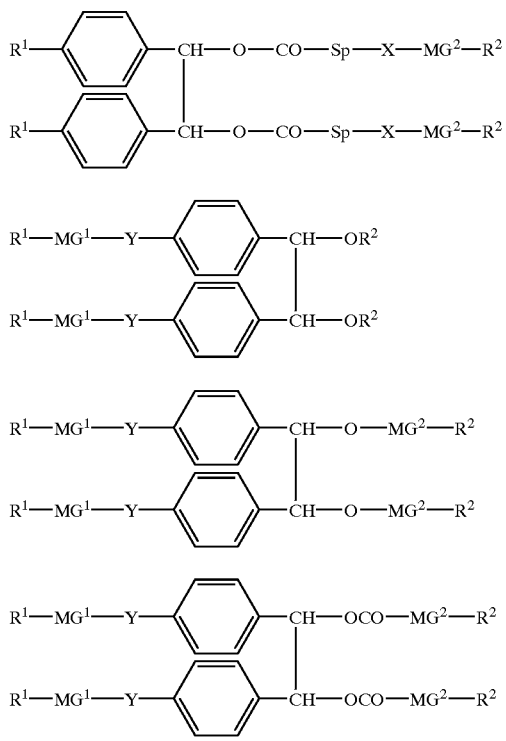

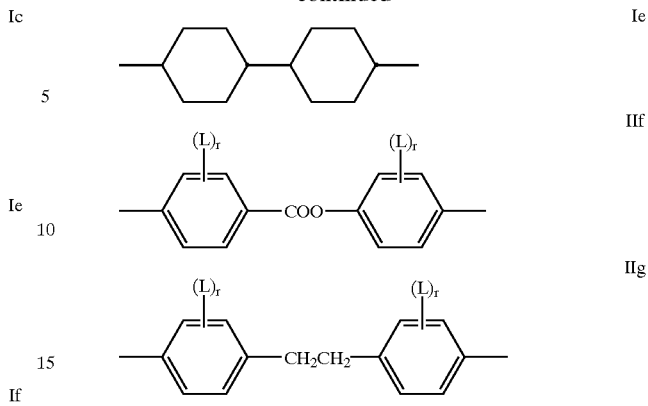

wherein $R^1$, $R^2$, $MG^1$, $MG^2$, Sp, X and Y have the meaning for the formula I.

19. A chiral compound according to claim 17, wherein at least one of groups $R^1$ and $R^2$ is alkyl or alkoxy with 1 to 12 C atoms.

20. A chiral compound according to claim 17, wherein $MG^1$ and $MG^2$ are independently selected from groups of the following formulea

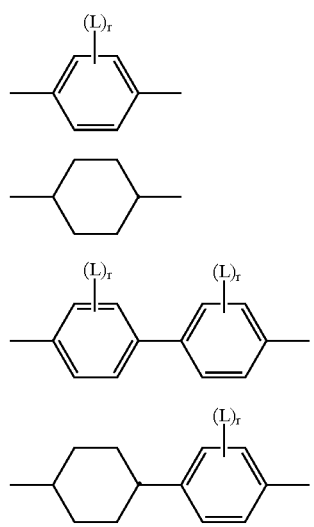

wherein L in each independently denotes halogen, a cyano or nitro group or an alkyl, alkoxy or alkanoyl group having 1 to 7 C atoms wherein one or more H atoms are optionally substituted by F or Cl and r is 0,1 or 2.

21. A liquid crystalline mixture comprising at least one chiral compound according to claim 17.

22. A polymerizable liquid crystalline mixture comprising at least one chiral compound according to formula I of claim 17 and at least one polymerizable mesogenic compound having at least one polymerizable functioning group which is not of formula I.

23. An anisotropic polymer film with a chiral liquid crystalline phase comprising at least one chiral compound according to claim 17.

24. The mixture of claim 8, wherein the polymerizble mesogenic compound having at least one polymerizable functional group is a compound of the formula V:

$$P\text{-}(Sp\text{-}X)_n\text{-}(A^1\text{-}Z)_m\text{-}A^2\text{-}R^5 \qquad V$$

wherein

P, Sp, X and n have the meaning of formula I, $A^1$, Z and m have the meaning of formula II, $A^2$ has one of the meanings of $A^1$, and $R^5$ has the meaning of $R^1$ in formula I.

25. The mixture if claim 22, wherein the polymerizable mesogenic compound having at least one polymerizable functional group is a compound of the formula V:

$$P\text{-}(Sp\text{-}X)_n\text{-}(A^1\text{-}Z)_m\text{-}A^2\text{-}R^5 \qquad V$$

wherein

P, Sp, X and n have the meaning of formula I, $A^1$, Z and m have the meaning of formula II, $A^2$ has one of the meanings of $A^1$, and $R^5$ has the meaning of $R^1$ in formula I.

26. A liquid crystalline mixture according to claim 7, wherein the mixture is thermochromic.

* * * * *

UNITED STATES PATENT AND TRADEMARK OFFICE
CERTIFICATE OF CORRECTION

PATENT NO. : 6,511,719 B2
DATED : January 28, 2003
INVENTOR(S) : Farrand et al.

It is certified that error appears in the above-identified patent and that said Letters Patent is hereby corrected as shown below:

Column 32,
Line 59, reads "optionally, being" should read -- optionally being --
Line 67, reads "II-12 to II-24" should read -- II-12 to II-27 --

Column 33,
Line 19, reads "-PheL-Z-PheL-Z-Phe" should read -- Phe-Z-PheL-Z-Phe --
Line 34, reads "cyclohxylene," should read -- cyclohexylene, --
Line 40, reads "formula II-4 of II-5," should read -- formula II-4 or II-5, --

Column 35,
Line 64, reads "atoms, -OCO-O-," should read -- atoms, X in each case independently denotes -O-, -S-, -CO-, -COO-, -OCO-O-, --
Line 66, reads "single bond, in each case" should read -- single bond, Y in each case --

Column 36,
Line 6, reads "a, b, c, and d" should read -- a, b, c and d --
Line 33, reads "-OCO-, -CH=CH-," should read -- -OCO-CH=CH --
Line 39, reads "non-adacent Ch2 groups" should read -- non-adjacent $CH_2$ groups --

Column 37,
Line 33, reads "for the" should read -- given for the --
Line 41, reads "formulea" should read -- formulae --

Column 38,
Line 19, reads "in each independently" should read -- in each case independently --
Line 22, reads "r is 0,1 or 2." should read -- r is 0, 1 or 2. --
Line 29, reads "polymerizable functioning" should read -- polymerizable functional --
Line 34, reads "polymerizble" should read -- polymerizable --

UNITED STATES PATENT AND TRADEMARK OFFICE
CERTIFICATE OF CORRECTION

PATENT NO. : 6,511,719 B2
DATED : January 28, 2003
INVENTOR(S) : Farrand et al.

It is certified that error appears in the above-identified patent and that said Letters Patent is hereby corrected as shown below:

<u>Column 38 (cont'd),</u>
Line 47, reads "mixture if claim" should read -- mixture of claim --

Signed and Sealed this

Sixth Day of July, 2004

JON W. DUDAS
*Acting Director of the United States Patent and Trademark Office*